United States Patent
Vilser et al.

(10) Patent No.: US 7,543,939 B2
(45) Date of Patent: Jun. 9, 2009

(54) DEVICE AND METHOD FOR RECORDING AND REPRESENTING IMAGES OF A TEST OBJECT

(75) Inventors: Walthard Vilser, Rudolstadt (DE); Bernd Ullrich Seifert, Griesheim (DE); Thomas Riemer, Jena (DE); Axel Fink, Ilmenau (DE)

(73) Assignee: IMEDOS GmbH, Jena (DE)

( * ) Notice: Subject to any disclaimer, the term of this patent is extended or adjusted under 35 U.S.C. 154(b) by 274 days.

(21) Appl. No.: 10/589,916

(22) PCT Filed: Feb. 16, 2005

(86) PCT No.: PCT/DE2005/000287

§ 371 (c)(1), (2), (4) Date: Aug. 18, 2006

(87) PCT Pub. No.: WO2005/079658

PCT Pub. Date: Sep. 1, 2005

(65) Prior Publication Data

US 2007/0179382 A1 Aug. 2, 2007

(30) Foreign Application Priority Data

Feb. 20, 2004 (DE) ................ 10 2004 008 675

(51) Int. Cl.
*A61B 3/14* (2006.01)
*A61B 3/10* (2006.01)

(52) U.S. Cl. ............... 351/206; 351/213; 351/221

(58) Field of Classification Search ............... 351/206, 351/207, 213
See application file for complete search history.

(56) References Cited

U.S. PATENT DOCUMENTS

| 4,279,478 | A | * | 7/1981 | Matsumura | ............... 351/206 |
| 4,877,322 | A | | 10/1989 | Hill | |
| 5,141,303 | A | | 8/1992 | Yamamoto et al. | |
| 5,318,022 | A | | 6/1994 | Taboada et al. | |
| 6,142,629 | A | * | 11/2000 | Adel et al. | ............... 351/206 |
| 6,364,829 | B1 | * | 4/2002 | Fulghum | ............... 600/160 |
| 6,478,424 | B1 | | 11/2002 | Grinvals et al. | |
| 2001/0033364 | A1 | | 10/2001 | Cabib et al. | |
| 2003/0091221 | A1 | * | 5/2003 | Marcelpoil et al. | ......... 382/128 |
| 2005/0010115 | A1 | * | 1/2005 | Bone et al. | ............... 600/476 |

FOREIGN PATENT DOCUMENTS

| DE | 38 18 278 | 2/1989 |
| DE | 198 35 067 | 11/2000 |

(Continued)

*Primary Examiner*—Jordan M. Schwartz
(74) *Attorney, Agent, or Firm*—Reed Smith LLP

(57) ABSTRACT

The invention relates to an illumination system comprising at least one beam path with means for simultaneously illuminating the test object within at least one reference wavelength range and at least one data wavelength range, each of which is coordinated with one respective color channel of an imaging recording system. The at least one data wavelength range is used for detecting a medically relevant piece of information while the at least one reference wavelength range is at least nearly invariant in relation to said medically relevant piece of information. The inventive method combines the image values of evaluation windows or individual pixels of simultaneously recorded images into secondary images and image sequences while generating location-resolved dynamic characteristic values which are combined into function images.

15 Claims, 5 Drawing Sheets

FOREIGN PATENT DOCUMENTS

| | | |
|---|---|---|
| EP | 0 397 377 | 11/1990 |
| WO | 88/03396 | 5/1988 |
| WO | 01/15597 | 3/2001 |
| WO | 02/053020 | 7/2002 |
| WO | 2004/096033 | 11/2004 |

* cited by examiner

DEVICE AND METHOD FOR RECORDING AND REPRESENTING IMAGES OF A TEST OBJECT

CROSS-REFERENCE TO RELATED APPLICATIONS

This application claims priority of International Application No. PCT/DE2005/000287, filed Feb. 16, 2005 and German Application No. 10 2004 008 675.3, filed Feb. 20, 2004, the complete disclosures of which are hereby incorporated by reference.

BACKGROUND OF THE INVENTION a) Field of the Invention

The invention is directed to an arrangement for recording and reproducing images of an object to be examined having an illumination system, an image-generating recording system, and a controlling and evaluating computer. The arrangement is suitable in particular for measurement systems for spectrometric examination of metabolism and of microcirculation which graphically display spatial or temporal differences in order to determine pathological changes or therapeutic changes in the object to be examined.

Further, the invention is directed to an image-generating method for detecting spatial and/or temporal, medically relevant differences in anatomical structures and functional characteristics of an object to be examined which is illuminated for image generation and selectively stimulated or provoked.

b) Discussion of the Related Art

For significant detection of pathological or therapeutic changes in the course of a disease, different methods for imaging the retina are employed within the framework of ophthalmologic diagnostics above all so that, apart from static information that is spatially resolved at a point in time, dynamic retina characteristic values can be obtained, with or without additional provocation or stimulation, from image sequences. In particular, these are systems for determining spectral temporal or spatial differences and systems for detecting microcirculation values and for functional imaging.

Due to different, uncomparable illumination situations within an image (varying spatial lighting) and between different images, e.g., a change in the main focus of illumination, occurrence of shadows or reflections during spontaneous eye movement, the determination of very slight changes in brightness, position and shape that is required for purposes of detection is subject to a high error rate which sometimes renders measurements useless.

Therefore, in a solution known from DE 38 18 278 C2, the differences in illumination are eliminated by scaling the video signals to the video signal of a reference wavelength. The stated object in DE 38 18 278 C2 is to substantially eliminate methodic and subjective errors in the evaluation and comparison of different images which are recorded at the same time or at different times. For the purpose of directly displaying image changes, the recording beam path is split by beamsplitters into at least two partial beam paths for one and the same image field of the eye, and means for selecting optical information are arranged in at least one partial beam path.

This optical concept is disadvantageous in particular because of the adjustments required for implementing the partial beam paths, the extremely high light stress to which the patient is subjected, and the fact that no simple constructional variants which would simplify the apparatus and reduce costs can be derived from the concept. In addition, the suggested technical solution for functional imaging can be used only conditionally.

OBJECT AND SUMMARY OF THE INVENTION

It is the primary object of the invention to record images of the object to be examined with reduced light stress and lower expenditure on adjustments and to generate secondary images which are substantially independent from brightness, are highly suitable for spectrometric studies of the metabolism and microcirculation in the eye as well as for functional imaging, and can be adapted to the medical inquiry and make it possible to provide complex secondary image information while also enabling simple, practicable and extremely economical constructional variants.

This object is met in an arrangement of the type mentioned above in that the illumination system contains at least one illumination beam path with means for simultaneous illumination of the object to be examined by at least one reference wavelength region and at least one information wavelength region, in that the image-generating recording system has at least two color channels, and the reference wavelength region and information wavelength region are adapted to one color channel each so as to be received by the latter, and in that the at least one reference wavelength region is at least approximately invariant with respect to medically relevant information from the object to be examined, and the at least one information wavelength region is provided for detecting the medically relevant information.

Adaptation to the color channels of the recording system, which is constructed, e.g., as a color camera, is preferably carried out in such a way that a wavelength region serving to illuminate the object to be examined is associated with each color channel.

The arrangement according to the invention which preferably serves as an image-generating basis for measurement systems and for functional imaging of metabolism and of microcirculation, in particular capillary vessel analysis, can be realized in a particularly simple manner and at reduced cost of apparatus on the illumination side, but can also be constructed as an embodiment form that can be accommodated to the medical inquiry adaptively.

The illumination burden is considerably reduced compared to DE 38 18 278 C2 by limiting the illumination radiation on the illumination side to spectral portions of the illumination radiation.

In a particularly advantageous construction of the invention which is conducive to low expenditure on apparatus, the means for simultaneous illumination of the object to be examined have a wavelength-selective optical filter device which is arranged in the illumination beam path for filtering the totality of illumination light that is radiated for illuminating the object to be examined. The filter device can be constructed as a layer filter whose layer construction realizes at least two narrow transmission regions serving as a reference wavelength region and an information wavelength region. The layer filter is particularly suitable for arrangement in a parallel beam portion of the illumination beam path.

Accordingly, known ophthalmologic imaging systems or, when using a color camera, conventional fundus cameras can be retrofitted in a particularly simple manner without forming separate beam paths and without expenditure on adjustment by way of the filter insert which is usually already provided.

The means for simultaneous illumination of the object to be examined can also have a wavelength-selective optical filter device which comprises sector-shaped filter areas and is arranged in the aperture plane or in a plane of the illumination beam path conjugate to the aperture plane for filtering the totality of illumination light that is radiated for the illumination of the object to be examined. In this connection, it is advantageous when the optical filter device comprises adjacent groups of filter areas and each group contains the filter areas for the wavelength regions to be selected.

Filters having the geometric structure mentioned above are especially advantageous in a novel conception of an imaging system or of a fundus camera.

In another construction of the invention, the means for simultaneous illumination of the object to be examined have at least two variously selecting optical bandpass filters whose selected wavelength regions form the reference wavelength region and information wavelength region. The bandpass filters are arranged in separate partial beam paths on the illumination side which proceed from a common illumination source and which are united to form a common beam path on the illumination side. At least one of the bandpass filters can be constructed as a spectrally tunable bandpass filter whose control is connected to the controlling computer. When the arrangement according to the invention is constructed in this way, an adaptive generation of secondary images is ensured in that the illumination bands can be advantageously adapted spectrally to the medical inquiry and to the color channels of the color camera, either by exchanging the bandpass filter or by means of computer-controlled adjustment of the spectrally tunable bandpass filter. Since the illumination-side partial beam paths come from a common illumination source, the intensity in the spectrally distinct partial beam paths can also be compensated by known devices and optimized for the recording conditions of the color camera.

The invention also includes an embodiment form in which the means for simultaneous illumination of the object to be examined have at least two illumination sources which emit in different wavelength regions and whose illumination light is combined in a common illumination beam path that is directed to the object to be examined in order to ensure identical geometric illumination characteristics. Also, it may be advantageous when one of the light sources is spectrally tunable.

Further, it may be advantageous to use a light source emitting in a plurality of spectral bands.

For optimal control of the image-generating recording system, suitable means are used to match the intensity of the reference wavelength region and information wavelength region to the color channels. The means for intensity matching can be designed for variable intensities and can have control units which are connected to the control computer so that the intensity matching between the wavelength regions can be carried out during operation.

Multiple-chip color cameras and single-chip color cameras can advantageously be provided as an image-generating recording system.

The arrangement according to the invention can also be advantageously combined with a device for stimulation or provocation of the object to be examined for carrying out functional imaging to study its time responses to biological or artificial perturbation as changes in the microcirculation or metabolism.

For this reason, it is provided in a special development of the invention that a controllable optical light manipulator communicating with the controlling and evaluating computer is arranged in the illumination beam path, and the intensity curve and/or time curve of a primary light coming from an illumination source is modified in a programmed manner by means of the controllable optical light manipulator, wherein the modification has a temporally defined relationship with the adjustments of the illumination source and of the image recording and image evaluation. Finally, a secondary light which is generated from the primary light by the modification is provided for illumination and for selective stimulation or provocation of the object to be examined.

Multifunctionality can be achieved by influencing the illumination by means of an individual element arranged in the illumination beam path in that the light characteristics of the light guided into the illumination beam path are changed so as to be adapted to function, so that there is no need to provide, e.g., a separate stimulating illuminator or to superimpose the latter by means of an additional beam path. It can be decided by means of the freely programmable control of the light modulator whether the light of the illumination source is used for illumination or for stimulation.

In a particularly advantageous manner, the arrangement according to the invention can be used to implement a method for detecting spatial and/or temporal medically relevant differences in anatomical structures of the eye as the object to be examined. This is carried out in that images of the anatomical structures are recorded simultaneously in the color channels associated with the reference wavelength region and information wavelength region provided on the illumination side. Secondary image values are generated from the images for at least one noise-reduced secondary image by combining the image values of image points that are conjugate to one another in the color channels, and these secondary image values are associated with the anatomical structures in the image in a positionally correct manner.

A method of this kind can be combined with forming of an evaluation window which is moved over the image and which comprises at least two adjacent image points whose gray values are combined by summing or averaging to form a window value before generating the secondary image values. The secondary image values are generated from conjugate window values of the color channels. The evaluation window can be moved over the image either by sliding or so as to be offset by more than one image point in each instance for a secondary image with reduced image points. The evaluation windows for the color channels can have different window sizes, and the secondary image values can be generated from window values whose window center points are conjugate to one another.

While an increasing number of image points within the evaluation window is connected with a reduction in the geometric resolution, the photometric resolution increases in an advantageous manner. At the same time, errors resulting from overlap errors caused by geometric manufacturing tolerances in the production of the photoelectric sensor surfaces are reduced.

By using the method according to the invention, high-resolution single-chip color cameras can also be used in an advantageous manner because the required image point correlation between the color channels combined with an increase in photometric accuracy and resolution can be brought about when a window is formed.

In a particularly advantageous embodiment of the method, a secondary image sequence is generated from successively generated secondary images of identical image sections and is stored at least temporarily until the evaluation is concluded. The secondary image sequence can be generated with video standard in continuous illumination light but also as a strobe sequence in one or more sessions over longer intervals of time. The secondary images belonging to an image sequence should be spatially oriented to one another based on the offset and/or rolling and/or distortion of the original images.

The secondary image sequences are especially suitable in that characteristic values describing the functions of metabolism, vision or microcirculation or temporal or spatial changes between the secondary values of a secondary image sequence can be determined from time sequences of the secondary image values of identical image points or combined image values of identical secondary image sections. Very informative functional images result because the secondary values are associated with the anatomical structures in the original image. Provoked or stimulated changes in metabolism, vision or microcirculation can also be advantageously recorded with the secondary image sequences.

The following are some examples of the numerous characteristic values for functional imaging that can be determined by the method according to the invention:

local capillary pulse volumes of blood local critical perfusion pressures from provoked intraocular pressure regions of blood volume, atrophy and ischemia (avascular zones without fluorescence angiograms) and dilation capacity and dilation dynamics of local capillary blood in response to flicker provocation dilation capacity and constriction capacity and dynamics of blood vessels in response to other vessel provocation and stimuli extent and dynamics of functionally caused spectral changes after stimulation or provocation of the vision function and metabolism characteristic values describing the extent and dynamics of changes in local oxygen saturation in response to provocation or stimulus of metabolism, blood flow and/or vision function.

Further, the method which can be implemented by the arrangement according to the invention can be designed in such a way that the reference wavelength region and information wavelength region can be changed during the generation of secondary image sequences by manually changing the wavelength-selective optical filter device or by controlling the spectrally tunable bandpass filters.

Finally, it is also possible to adapt the intensities of the reference wavelength region and information wavelength region manually or through the control computer during the generation of secondary image sequences in that feedback signals which control and optimize the matching of intensities are formed from the gray values of the color channels or from the secondary image values.

Temporal and spatial changes, for example, in blood volume, oxygen saturation or different material concentrations such as pigments can be displayed by matching the spectral characteristic of the transmission wavelengths. However, by means of secondary images of a plurality of individual recordings each with the same reference wavelength but different information wavelengths, different spectrally overlapping material concentrations or layer thicknesses can also be determined in a known manner and displayed in a false-color-coded image, e.g., the oxygen saturation. It is preferable to use more than two wavelength regions which are calculated to form a complex secondary image.

In order to bring out spatial changes in the secondary images, conventional methods of image analysis can be applied to the secondary image, e.g., subtraction, threshold techniques or false color coding or particle tracking techniques for determining particle velocities and their vector fields.

The pulse volume, pulse shape, pulse phase displacement, cell velocity and velocity vector and cell flow can be determined from the secondary image sequences as a function of image location and can be compiled to form measurement value images (measurement value mapping).

Further, the above-stated object is met, according to the invention, by a method of the type mentioned in the beginning in which the object to be examined is illuminated simultaneously by at least two wavelength regions of an illumination beam which are adapted each to one color channel of a color camera serving to record images, wherein one of the wavelength regions is at least approximately invariant with respect to medically relevant information, and another wavelength region is provided for detecting the medically relevant information, and in which at least one secondary image is generated from at least two images of the anatomical structures in that secondary image values which are associated in a positionally correct manner with the anatomical structures in one of the images are generated from image values of image points that are conjugate to one another in the color channels.

A method of this kind can be combined with the forming of an evaluation window for each color channel. This evaluation window is moved over the image and comprises at least two adjacent image points whose gray values are combined by summing or averaging to form a window value before generating the secondary image values. The secondary image values are generated from conjugate window values of the color channels. The evaluation window can be moved over the image either by sliding or so as to be offset by more than one image point in each instance for a secondary image with reduced image points. The evaluation windows for the color channels can have different window sizes, and the secondary image values can be generated from window values whose window center points are conjugate to one another. As was already stated, the evaluation window can be moved over the image either by sliding or so as to be offset by more than one image point in each instance for a secondary image with reduced image points.

Linking of image values of conjugate pixels or evaluation windows between the color channels is preferably carried out by division resulting in brightness-independent secondary images.

The invention will be explained more fully in the following with reference to the schematic drawings.

DESCRIPTION OF THE PREFERRED EMBODIMENTS

Figure 1:
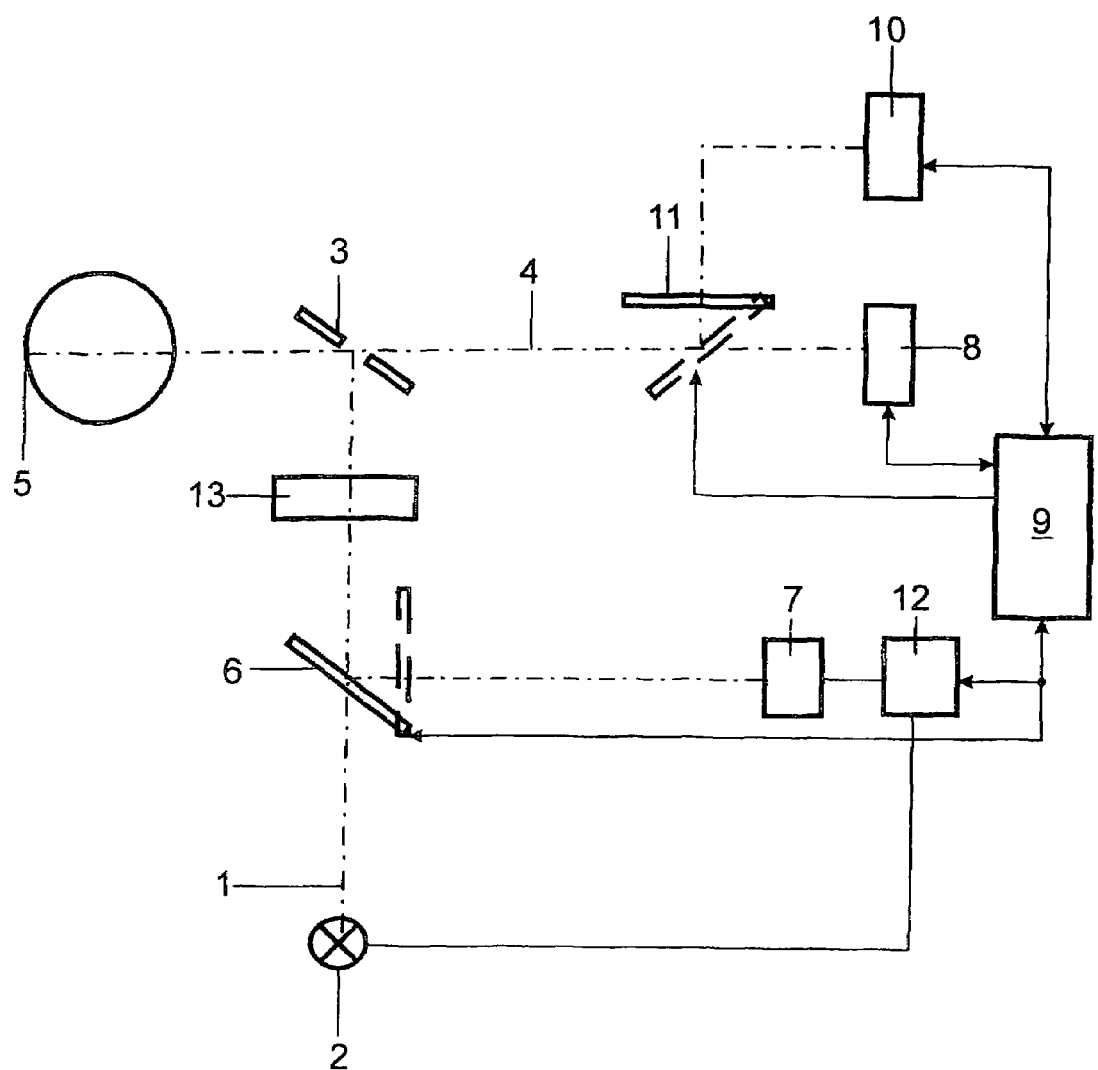
FIG. 1 shows a simplified view of the construction of a first embodiment of the arrangement according to the invention.

The first embodiment example shows a simple and distinctly economical construction according to the invention for displaying blood volume independent from brightness. The arrangement comprises the elements of any retina camera, wherein a filter 13 according to the invention which is spectrally adapted according to the invention to an electronic color camera 8 as will be described in the following is arranged in a common illumination beam path 1 of an illumination system containing at least one illumination source 2. The electronic images are supplied to a controlling and evaluating unit, e.g., a controlling and evaluating computer 9, which serves to generate and display secondary images and functional images and to store them advantageously in a patient-specific manner. The other elements in FIG. 1 which form the illumination beam path 1 and the recording beam path 4 are known from retina camera technology. The elements include a perforated mirror 3, a recording beam path 4 passing through its central opening. The illumination light is directed through optically imaging elements, not shown here, to the object to be examined, in this case the fundus of the eye 5, through an area surrounding the central opening. Light reflected by the fundus 5 passes via the recording beam path 4 and via optically imaging elements, also not shown, to an image-generating recording system. In the present embodiment example, the color camera 8 is provided for this purpose. The camera control of the color camera 8 is connected to the central controlling and evaluating unit, particularly the controlling and evaluating computer 9. A power supply 12 serving to supply power to the two illumination sources 2 and 7 is connected to the controlling and evaluating computer 9 and likewise corresponding tilting mirror controls.

With regard to the invention, it is not important whether only one continuous illumination source 2 or only one strobe illumination source 7 is provided or whether the two sources are used together as in FIG. 1. Also irrelevant with regard to the invention is the manner of coupling into the common illumination beam path 1 which is carried out in a conventional manner via a swing-out mirror 6 in this instance. Also, another recording beam path with another camera 10 which is likewise controlled by computer via a tilting mirror 11 and can be provided as an alternative to image recording with the color camera 8, depending on the examination to be performed, is also not absolutely required for the invention.

The images of the color channels of the reference wavelength region and information wavelength region are processed to form secondary images corresponding to the method according to the invention. For this purpose, evaluation windows are formed in the individual channels of each color image and its image values are summed to form a window image value. The conjugate window image values of the images in the individual color channels of a simultaneously recorded color image are divided by one another and give secondary image values that are combined in an image-correct manner to form secondary images. For this purpose, the evaluation windows are moved over the images. The size of the evaluation windows is not initially relevant to the invention; nor is the calculation of the window values and secondary image values, since this calculation can be carried out very differently according to the application. Different application programs determine the calculation rules and window sizes in accordance with the medical inquiry. The formation of the described quotient-formers from the window values presents an advantageous design leading to the brightness-independent secondary images. By means of the swing-out mirror 6, continuous sequences of images can be recorded selectively with the continuous illumination source 2 or strobed color images can be recorded from which discontinuous secondary image sequences or individual secondary images or continuous secondary image sequences can be generated.

The evaluation of individual strobed secondary images can be used to show spatial changes in the blood volume, e.g., for finding avascular regions in the fundus or ischemic regions on the papilla. Since the secondary images are brightness-independent, this embodiment example can be used to quantify and document pathological or therapeutic changes between different sessions with high reproducibility. Examples include the early detection of incipient pallor of the optic disk or quantification of atrophic papillary alterations and changes thereof, e.g., in glaucoma.

Strobed or Continuous Image Sequences: Another possible application is the recording of strobed image sequences or continuous image sequences for functional imaging. The time curves of individual or combined secondary image values from the image sequences are evaluated, and clinically relevant characteristic values of the time curves are calculated and are then displayed again in compiled form in an image-correct manner in functional images. Characteristic values of this type are advantageously formed in such a way that they describe functions. For example, the pulse amplitude of capillary, pre-capillary, and post-capillary retinal vessels and changes therein can be determined before and after events or provocations or in the course of a disease or therapy and can be compiled in a functional image in a spatially resolved manner. In this connection, it can be advantageous to combine the arrangement according to the invention with a provocation method, e.g., with an ophthalmic ocular dynamometer for increasing the intraocular pressure by means of a suction cup. Avascular capillary zones which could otherwise only be determined by means of invasive fluorescence angiography can now be detected non-invasively and can be spatially delimited in the functional images. By showing the pulse amplitudes under increased intraocular pressure in glaucoma or by means of a provoked (artificial) increase, the spatial correlation and delimitation of critical perfusion pressures can be shown based on collapsing pulsation amplitudes, and the detection of brain pressure values, among others, can be objectified.

Figure 2:
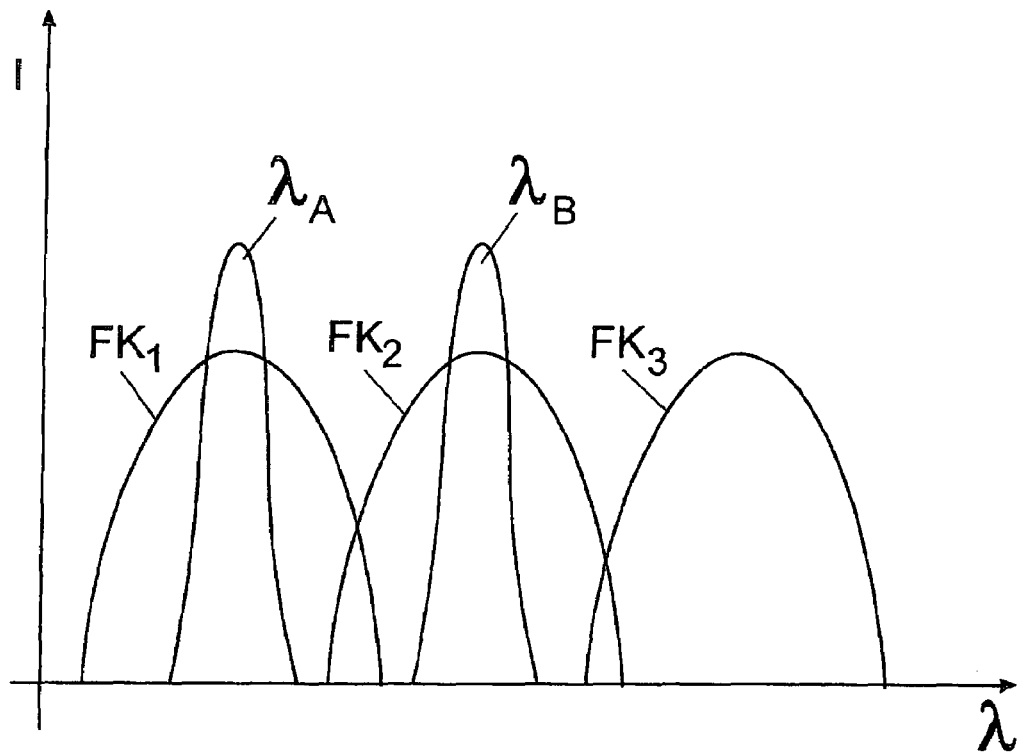
FIG. 2 shows the position of selected wavelength regions in the color channels when the wavelength regions which are prepared on the illumination side are adapted to the color channels with respect to a matching of colors.

According to the invention, based on the spectral characteristic of the color camera 8, a filter 13 is used in the illumination beam path 1. The filter 13 generates at least two wavelength regions $\lambda_i$ (i=A, B, C) as a reference wavelength region and an information wavelength region for simultaneous differently colored illumination of the object to be examined, each of these reference and information wavelength regions being adapted, respectively, to one of the color channels $FK_j$ (j=1, 2, 3) of the color camera 8 with respect to a color matching corresponding to FIG. 2.

Insofar as it is possible to correlate the wavelength regions $\lambda_i$ with the color channels $FK_j$ in an unambiguous manner and when a color channel $FK_j$ receives color signal components from an unassociated wavelength region $\lambda_i$, erroneous interpretations due to these intersections of regions can be avoided by adding another wavelength region $\lambda_i$.

Suitable optical filters 13 are layer filters such as dual bandpass filters or triple bandpass filters or a geometrically structured filter comprising sector-shaped filter regions KS with different spectral filter characteristics whose sectors can have identical or different sector surface contents.

While the former are particularly suitable for subsequent integration in the illumination beam path 1 of already existing systems, preferably in a parallel beam portion, the sector filters with geometric color composition have the advantage that they can be produced in a simple manner without elaborate layer calculation. Also, the intensities of the wavelength regions $\lambda_i$ provided for illumination can be controlled in a simple manner with these filters by means of the size of the sector surfaces. However, it is necessary for the intended bandpass filter effect of the sector filters that they can be arranged in the vicinity of the aperture plane so that the illumination light passing through the filter 13 illuminates the entire image field without imaging the colors, in this case on the fundus 5.

Figure 3:
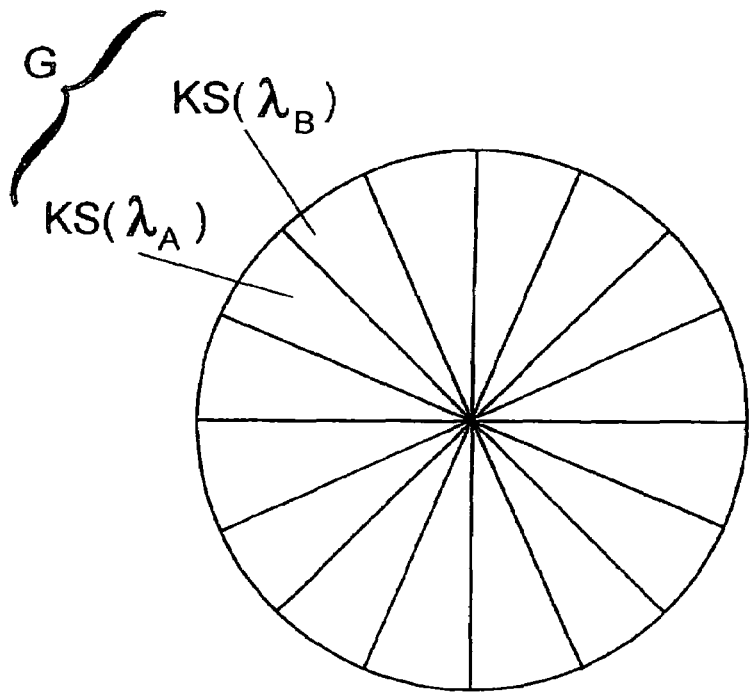
FIG. 3 shows a geometrically structured filter composed of sector-shaped filter regions with different filter characteristics.

Further, the sector-shaped filter areas KS should be arranged in an alternating manner in the most highly graduated pattern possible corresponding to the quantity of wavelength regions $\lambda_i$ that is provided (FIG. 3). The filter regions KS are arranged adjacent to one another in groups G corresponding to the quantity of wavelength regions $\lambda_i$. In the simplest case where two wavelength regions $\lambda_A$ and $\lambda_B$ are provided, two different filter regions KS ($\lambda_A$) an KS ($\lambda_B$) alternate with one another. This applies in a corresponding manner by groups of three to three wavelength regions $\lambda_A$, $\lambda_B$ and $\lambda_C$.

Accordingly, erroneous measurements can be prevented when the entrance pupil is displaced relative to the object to be examined by bringing the arrangement out of center. When the filtering sectors are distributed over a large surface, there is a risk that different color components will overlap different areas of the object to be examined resulting in severe errors when detecting the intensity ratios.

The sector filters have the further advantage that the intensity of the wavelength regions $\lambda_i$ can be controlled within an extensive range by the size of the sector surfaces relative to one another. Equality of intensities can be produced, but when it is required by the fundus 5 as object to be examined, a difference in intensities can also be produced.

This effect can be achieved in the layer filters when additional means are provided in the illumination beam path 1 or in the recording beam path 4 for intensity attenuation depending upon wavelength region, e.g., edge filters for selective adjustment.

According to the invention, multi-chip color cameras or single-chip color cameras can be used as color cameras.

Single-chip color cameras, in which mosaic filters define red-sensitive, green-sensitive and blue-sensitive pixels on the CCD element and a color image point comprises a combination of green-sensitive, red-sensitive and blue-sensitive pixels, are suitable as color cameras for the application of the invention when the size of a color image point corresponds to the size of the smallest structure to be detected or processed.

On one hand, single-chip color cameras have the advantage that they are economical. On the other hand, they have a substantially greater quantity of pixels in comparison to multi-chip color cameras so that, by reducing the existing high geometric resolution if necessary, it is possible to achieve a high photometric resolution by assembling a plurality of color image points to form a photometric measurement point by summing or averaging these color image points. For this purpose, it is necessary that the color contents of the structures present in the object to be examined are correctly reproduced based on a stochastic distribution. A photometric resolution suitable for a capillary functional image can be achieved in this way.

Figure 4:
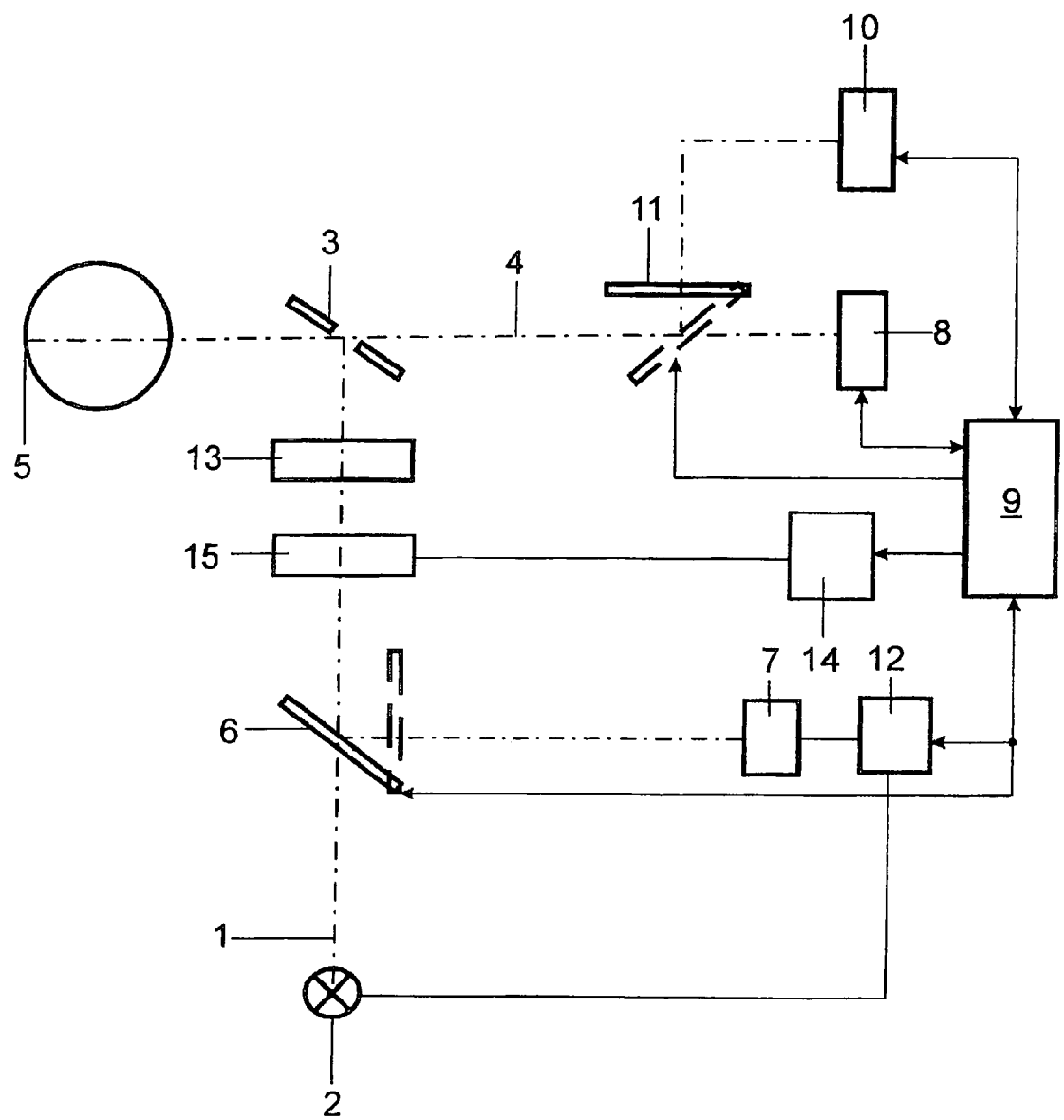
FIG. 4 shows the arrangement according to the invention from FIG. 1 with an additional device for stimulation or provocation of the object to be examined.

According to FIG. 4, in a second embodiment of the invention, an optical light manipulator 15 which is controllably connected to an electronic control module 14 is arranged in the common illumination beam path 1 in addition to the filter 13. The control module 14 has an interface to the controlling and evaluating computer 9.

The light manipulator 15 which is controllable in a variety of ways by programming is a shared element which is available to all of the illumination sources and which, by modifying primary light, in this case the continuously emitting illumination source 2 and the strobe illumination source 7, generates secondary light for illumination and/or, optionally, for stimulation or provocation corresponding to the programmed control of the light modulator 15.

Accordingly, by influencing the illumination by means of an individual element arranged in the illumination beam path, multifunctionality can be achieved by changing the light characteristics of the light guided in the illumination beam path so as to be adapted to function.

Figure 5:
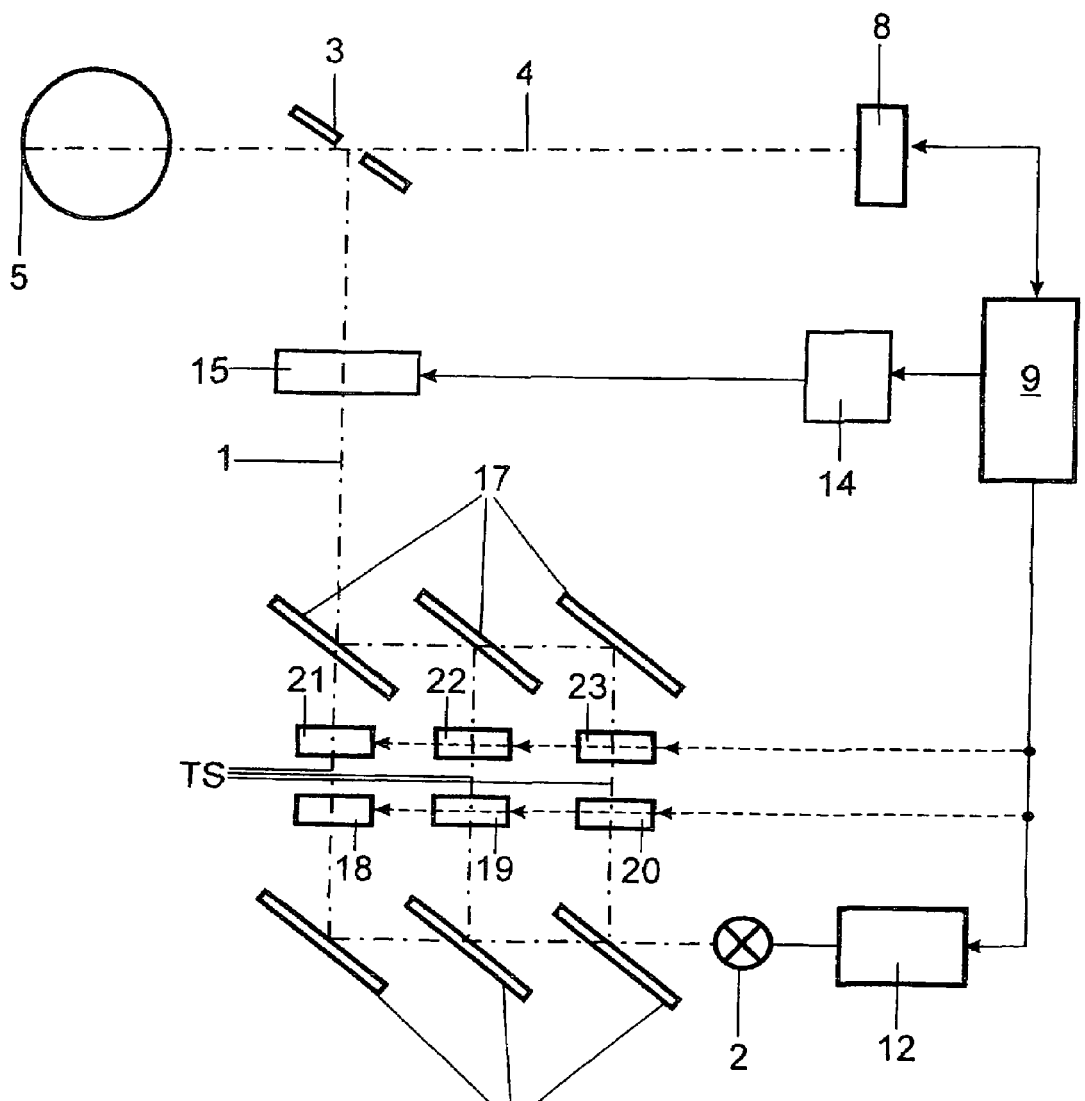
FIG. 5 shows a simplified view of a third embodiment of the arrangement according to the invention.

In the construction of the arrangement according to the invention shown in FIG. 5, a beamsplitter is arranged in front in the illumination beam path 1. By means of this beamsplitter, the illumination light is split through spectral splitter 16 into identical proportions in partial beam paths TS and is subsequently combined again through spectral splitter 17. By means of the spectral splitting, the illumination light in the partial beam paths TS has different spectral characteristics which are adapted, respectively, by means of bandpass filters 18, 19, 20 arranged in the partial beam paths TS, to one of the color channels $FK_j$ (j=1, 2, 3) of the color camera 8 with respect to color matching corresponding to FIG. 2.

The bandpass filters 18, 19, 20 can either have fixed spectrally selecting characteristics and be exchangeable or are constructed as spectrally tunable bandpass filters whose controls are connected to the controlling and evaluating computer 9. Due to the resulting capability of tuning the spectral regions during operation of the arrangement according to the invention, image sequences can be recorded with spectrally different filter combinations.

Further, arranged in the partial beam paths TS are means for intensity matching in the form of attenuating filters 21, 22, 23 by which the spectrally different partial beams can be adapted to the color channels $FK_j$ of the color camera so that they are situated in approximately the same gray value range. The intensity matching can also be controllable by means of the controlling and evaluating computer 9, for which purpose the controls of the filters 21, 22, 23 are connected to the latter.

Figure 6:
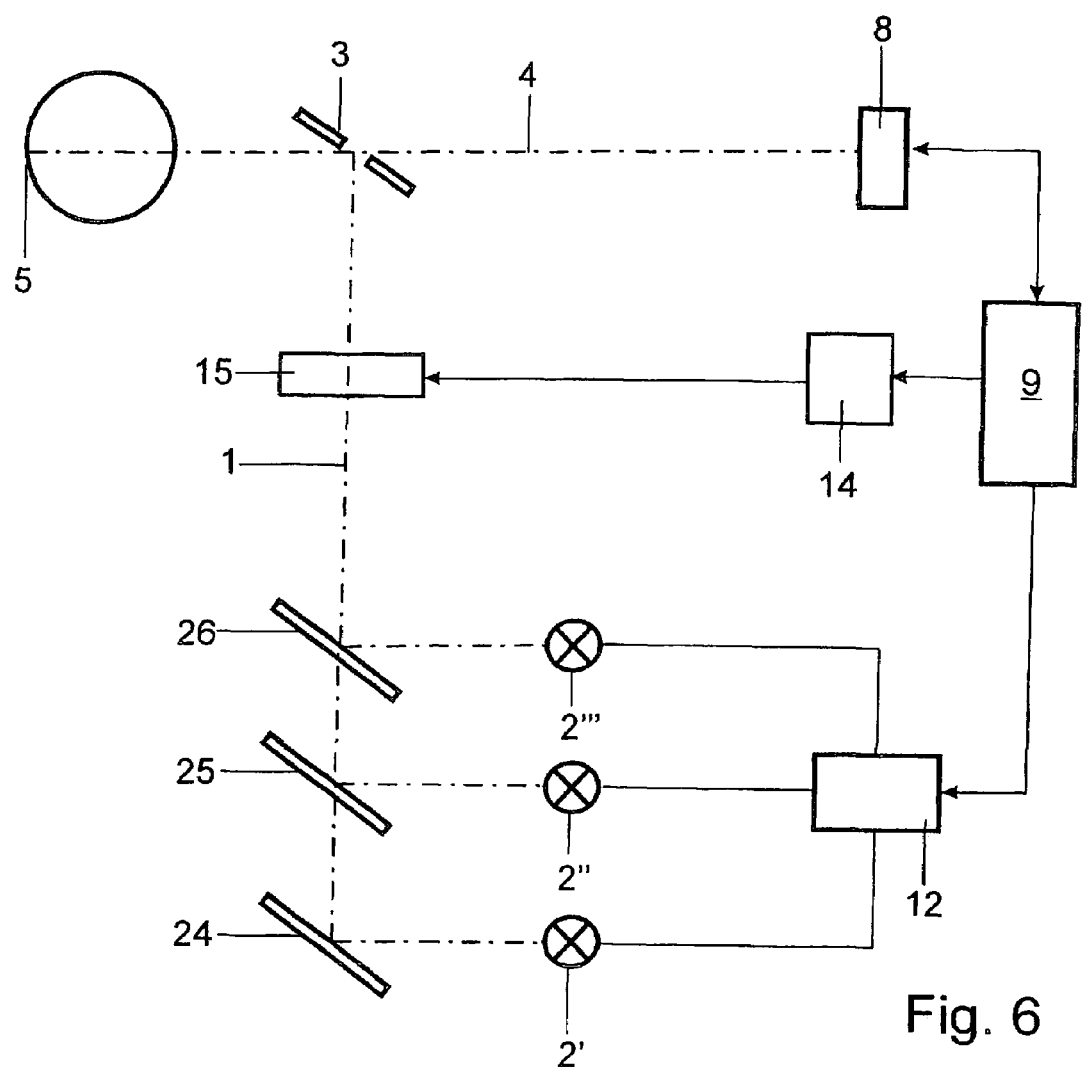
FIG. 6 shows a simplified view of a fourth embodiment of the arrangement according to the invention.

In the construction of the arrangement according to the invention shown in FIG. 6, illumination light from illumination sources 2', 2'', 2''' emitting in different spectra is coupled into the illumination beam path 1, which is directed to the object to be examined, by in-coupling mirrors 24, 25, 26 in order to ensure identical geometric illumination characteristics. The illumination sources 2', 2'', 2''' are controllable by means of the controlling and evaluating computer 9 in that their power supply 12 is connected to the latter. The light sources can be continuous light sources or light sources working in strobe mode.

According to the invention, in an alternating manner by means of a process control, stimulation can be carried out by a light manipulator 15, and the above-described illumination and recording, according to the invention, can be carried out subsequently or during stimulation.

One or more elements can be made controllable by means of the controlling and evaluating computer 9 in an advantageous manner. These elements include the spectral splitters 16, 17 from FIG. 5 or the in-coupling mirrors 24 to 26 which are then constructed as swing-out mirrors. The advantage consists in that the provided stimulation light and the recording light can be composed differently. This considerable expansion of possible applications by varying the spectral regions is further enhanced by forming at least one filter as a controllable spectral filter.

According to the invention, a feedback can be produced between signals of the color camera channels for adjusting the light-attenuating filters 21, 22, 23, by means of which the spectral components for an optimal camera control can be optimized while taking into account the individual measurement conditions and the characteristics of the patient's eye. Use of filters for adapting or optimizing individual color channels, e.g., the use of color glass filters for reducing the infrared/red component, is known. The use of electronically controllable intensity-attenuating elements in the color channels, by which the color matching can be changed during the operation of the arrangement, has the advantage that optimal adjustments can be achieved for different regions of the fundus (papilla, macula and the rest of the fundus areas) in succession depending on the focus of the examination. The advantage of the last embodiment examples over the simple example according to FIG. 1 consists in the high degree of functional and individual adaptavity of the solution according to the invention.

While the foregoing description and drawings represent the present invention, it will be obvious to those skilled in the art that various changes may be made therein without departing from the true spirit and scope of the present invention.

What is claimed is:

1. An arrangement for recording and reproducing images of an object to be examined comprising:
   an illumination system;
   an image-generating recording system;
   a controlling and evaluating computer;
   said illumination system containing, in an illumination beam path, means for selecting at least one reference wavelength region and at least one information wavelength region from the beam of an individual illumination source in order to illuminate an object to be examined simultaneously by at least one reference wavelength region and at least one information wavelength region;
   said image-generating recording system comprising an image-recording camera;
   said reference wavelength region and information wavelength region each being adapted, respectively, to a color channel of the camera so as to be received by the color channel; and
   said at least one information wavelength region being provided for detecting medically relevant information from the object to be examined;
   wherein at least one device for stimulation or provocation of the object to be examined is provided for carrying out functional imaging; and
   wherein a controllable optical light manipulator communicating with the controlling and evaluating computer is arranged in the illumination beam path for programmable modification of the intensity curve and/or time curve of a primary light coming from an illumination source, in that the modification has a temporally defined relationship with the adjustments of the illumination source and of the image recording and image evaluation, and in that a secondary light which is generated from the primary light by the modification is provided for illumination and for selective stimulation or provocation of the object to be examined.

2. A method for detecting spatial and/or temporal medically relevant differences in anatomical structures of the eye as the object to be examined by means of an arrangement according to claim 1, comprising the steps of:
   recording images of the anatomical structures simultaneously in the color channels of an image-recording camera which are associated with the reference wavelength region and information wavelength region provided on the illumination side from the illumination beam of an individual illumination source; and
   generating secondary image values from the images for at least one noise-reduced secondary image by combining the image values of image points that are conjugate to one another in the color channels, and said secondary image values being associated with the anatomical structures in the image in a positionally correct manner;
   wherein an evaluation window is formed at least for one color channel, which evaluation window is moved over the image and comprises at least two adjacent image points whose gray values are combined by summing or averaging to form a window value before generating the secondary image values, and wherein the secondary image values are generated from window values of the color channels that are conjugate to one another with respect to their window center points or from pixels of the color channels.

3. The method according to claim 2, wherein the evaluation window is moved over the image by sliding and with window center points that are conjugate to one another.

4. The method according to claim 2, wherein the evaluation window is moved over the image so as to be offset by more than one pixel in each instance, and a secondary image with reduced image points is accordingly generated.

5. The method according to claim 2, wherein the evaluation windows for the color channels have different window sizes, and the secondary image values are generated from window values whose window center points are conjugate to one another.

6. The method according to claim 2, wherein the linking of the image values of the evaluation windows that are conjugate to one another or pixels is carried out by division.

7. The method according to claim 2, wherein a secondary image sequence is generated from successively generated secondary images of identical image sections and is stored at least temporarily until the evaluation is concluded, wherein the secondary image sequence is generated with video standard in continuous illumination light but also as a strobe sequence in one or more sessions over longer intervals of time.

8. The method according to claim 7, wherein the secondary images belonging to an image sequence are spatially oriented to one another based on the offset and/or rolling and/or distortion of the original images.

9. The method according to claim 7, wherein characteristic values describing the functions of metabolism, vision or microcirculation or temporal or spatial changes between the secondary values of a secondary image sequence are determined from the secondary image sequences.

10. The method according to claim 8, wherein characteristic values describing the functions of metabolism, vision or microcirculation or temporal or spatial changes between the secondary values of a secondary image sequence are determined from the secondary image sequences.

11. The method according to claim 10, wherein the characteristic values are associated with the anatomical structures in the original image in order to form functional images.

12. The method according to claim 7, wherein provoked or stimulated changes in metabolism, vision or microcirculation are recorded with the secondary image sequences.

13. The method according to claim 7, wherein the reference wavelength region and information wavelength region are changed during the generation of secondary image sequences by manually changing a wavelength-selective optical filter device or by controlling spectrally tunable bandpass filters.

14. The method according to claim 7, wherein the matching of the intensities of the reference wavelength region and information wavelength region is carried out manually or through the control computer during the generation of secondary image sequences in that feedback signals which control and optimize matching of intensities are formed from the gray values of the color channels or from the secondary image values.

15. An image-generating method for detecting spatial and/or temporal medically relevant differences in anatomical structures and functional characteristics of an object to be examined which is illuminated to form images and is optionally stimulated or provoked, comprising the steps of:

simultaneously illuminating the object to be examined by at least two wavelength regions which are generated from the illumination beam of an individual illumination source and which are adapted each to one color channel of a color camera serving to record images, wherein one of the wavelength regions is provided for detecting medically relevant information; and generating at least one secondary image from at least two images of the anatomical structures and generating secondary image values which are associated in a positionally correct manner with the anatomical structures in one of the images being generated from image values of image points that are conjugate to one another in the color channels;

wherein an evaluation window which is moved over the image is formed for each color channel, which evaluation window comprises at least two adjacent image points whose gray values are combined by summing or averaging to form a window value, and wherein the secondary image values are generated from window values of the color channels, which window values are conjugate to one another.

* * * * *